US010942107B2

(12) United States Patent
Wei et al.

(10) Patent No.: US 10,942,107 B2
(45) Date of Patent: Mar. 9, 2021

(54) METHODS OF SCREENING FOR MILD SKIN CLEANSER

(71) Applicant: The Procter & Gamble Company, Cincinnati, OH (US)

(72) Inventors: Karl Shiqing Wei, Mason, OH (US); Wei Ji, Cincinnati, OH (US); Marc Andrew Mamak, Mason, OH (US); Peter Joseph Stoffolano, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 222 days.

(21) Appl. No.: 16/211,531

(22) Filed: Dec. 6, 2018

(65) Prior Publication Data
US 2019/0178774 A1    Jun. 13, 2019

Related U.S. Application Data

(60) Provisional application No. 62/596,155, filed on Dec. 8, 2017.

(51) Int. Cl.
G01N 15/06    (2006.01)
A61K 8/02    (2006.01)
(Continued)

(52) U.S. Cl.
CPC .......... *G01N 15/06* (2013.01); *A61K 8/0291* (2013.01); *A61K 8/14* (2013.01); *A61K 8/31* (2013.01); *A61K 8/342* (2013.01); *A61K 8/361* (2013.01); *A61K 8/37* (2013.01); *A61K 8/375* (2013.01); *A61K 8/463* (2013.01); *A61K 8/85* (2013.01); *A61K 8/922* (2013.01); *A61Q 19/10* (2013.01); *G01N 15/0211* (2013.01);
(Continued)

(58) Field of Classification Search
CPC ............... G01N 15/06; G01N 15/0211; G01N 2015/0222; G01N 2015/0038; G01N 2015/0693; A61K 8/0291; A61K 8/14; A61K 8/31; A61K 8/342; A61K 8/361; A61K 8/37; A61K 8/375; A61K 8/463; A61K 8/85; A61K 8/922; A61Q 19/10
USPC ......................................... 436/149
See application file for complete search history.

(56) References Cited

U.S. PATENT DOCUMENTS 2,438,091 A    3/1948   Lynch
2,528,378 A    10/1950  McCabe, Jr.
(Continued)

FOREIGN PATENT DOCUMENTS

DE    102008035172 A1    2/2010
EP    1383542 B1    4/2008
(Continued)

OTHER PUBLICATIONS

Tate Owen, Roger Pynn, Jennifer S. Martinez, and Alison Butler; Micelle-to-Vesicle Transition of an Iron-Chelating Microbial Surfactant, Marinobactin E; Nov. 12, 2005; Langmuir, 21,26, 12109-12114 (Year: 2005).*
(Continued)

Primary Examiner — Jennifer Wecker
Assistant Examiner — Jonathan Bortoli
(74) Attorney, Agent, or Firm — John G. Powell

(57) ABSTRACT

Methods for screening skin cleansers for mildness can include utilization of a volume ratio of vesicles to micelles.

17 Claims, 5 Drawing Sheets

(51) Int. Cl.
*A61K 8/14* (2006.01)
*A61K 8/31* (2006.01)
*A61K 8/34* (2006.01)
*A61K 8/36* (2006.01)
*A61K 8/37* (2006.01)
*A61K 8/46* (2006.01)
*A61K 8/85* (2006.01)
*A61K 8/92* (2006.01)
*A61Q 19/10* (2006.01)
*G01N 15/02* (2006.01)
*G01N 15/00* (2006.01)

(52) U.S. Cl.
CPC ............... *G01N 2015/0038* (2013.01); *G01N 2015/0222* (2013.01); *G01N 2015/0693* (2013.01)

(56) References Cited

U.S. PATENT DOCUMENTS

| | | | |
|---|---|---|---|
| 2,658,072 | A | 11/1953 | Kosmin |
| 3,915,921 | A | 10/1975 | Schlatzer, Jr. |
| 3,940,351 | A | 2/1976 | Schlatzer, Jr. |
| 4,062,817 | A | 12/1977 | Westerman |
| 4,429,097 | A | 1/1984 | Chang et al. |
| 5,011,681 | A | 4/1991 | Ciotti et al. |
| 5,147,576 | A | 9/1992 | Montague et al. |
| 5,364,617 | A | 11/1994 | Bush et al. |
| 5,462,963 | A | 10/1995 | Bush et al. |
| 5,487,884 | A | 1/1996 | Bissett et al. |
| 5,652,228 | A | 7/1997 | Bissett |
| 5,681,852 | A | 10/1997 | Bissett |
| 5,965,502 | A | 10/1999 | Balzer |
| 6,068,834 | A | 5/2000 | Kvalnes et al. |
| 6,150,312 | A | 11/2000 | Puvvada et al. |
| 6,217,888 | B1 | 4/2001 | Oblong et al. |
| 6,395,691 | B1 | 5/2002 | Tsaur |
| 6,433,061 | B1 | 8/2002 | Marchant et al. |
| 6,537,527 | B1 | 3/2003 | Kvalnes et al. |
| 6,635,702 | B1 | 10/2003 | Schmucker-Castner et al. |
| 6,645,511 | B2 | 11/2003 | Aronson et al. |
| 6,759,376 | B2 | 7/2004 | Zhang et al. |
| 6,780,826 | B2 | 8/2004 | Zhang et al. |
| 6,897,253 | B2 | 5/2005 | Schmucker-Castner et al. |
| 7,084,104 | B2 | 8/2006 | Martin et al. |
| 7,098,180 | B2 | 8/2006 | Ganopolsky et al. |
| 7,119,059 | B2 | 10/2006 | Librizzi et al. |
| 7,157,414 | B2 | 1/2007 | Librizzi et al. |
| 7,488,707 | B2 | 2/2009 | Frantz et al. |
| 7,511,003 | B2 | 3/2009 | Focht et al. |
| 7,527,077 | B2 | 5/2009 | McCall et al. |
| 7,531,497 | B2 | 5/2009 | Midha et al. |
| 7,649,047 | B2 | 1/2010 | Tamareselvy et al. |
| 7,666,825 | B2 | 2/2010 | Wagner et al. |
| 7,754,666 | B2 | 7/2010 | Walters et al. |
| 7,763,419 | B2 | 7/2010 | Hendrix et al. |
| 7,767,389 | B2 | 8/2010 | Hendrix et al. |
| 7,771,924 | B2 | 8/2010 | Hendrix et al. |
| 7,771,925 | B2 | 8/2010 | Hendrix et al. |
| 8,067,517 | B2 | 11/2011 | Yoshinaka et al. |
| 8,105,996 | B2 | 1/2012 | Wei et al. |
| 8,309,667 | B2 | 11/2012 | Yoshinaka et al. |
| 9,750,674 | B2 | 9/2017 | Wei et al. |
| 10,085,924 | B2 | 10/2018 | Wei |
| 2004/0092415 | A1 | 5/2004 | Focht et al. |
| 2004/0223929 | A1 | 11/2004 | Clapp et al. |
| 2004/0223991 | A1 | 11/2004 | Wei et al. |
| 2004/0235702 | A1 | 11/2004 | Hawkins |
| 2005/0019299 | A1 | 1/2005 | LiBrizzi et al. |
| 2005/0020468 | A1 | 1/2005 | Frantz et al. |
| 2005/0049172 | A1 | 3/2005 | Lukenbach et al. |
| 2005/0075256 | A1 | 4/2005 | Librizzi et al. |
| 2005/0100570 | A1 | 5/2005 | Wei et al. |
| 2005/0276768 | A1 | 12/2005 | Wei et al. |
| 2006/0040834 | A1 | 2/2006 | Hilliard, Jr. et al. |
| 2006/0079419 | A1 | 4/2006 | Wagner et al. |
| 2006/0079420 | A1 | 4/2006 | Wagner et al. |
| 2006/0079421 | A1 | 4/2006 | Wagner et al. |
| 2006/0182699 | A1 | 8/2006 | Taylor et al. |
| 2006/0189495 | A1 | 8/2006 | LiBrizzi et al. |
| 2007/0155637 | A1 | 7/2007 | Smith, III et al. |
| 2007/0196344 | A1 | 8/2007 | Osborne et al. |
| 2007/0224696 | A1 | 9/2007 | Honkonen et al. |
| 2007/0286832 | A1 | 12/2007 | Clapp et al. |
| 2008/0095733 | A1 | 4/2008 | Griffin et al. |
| 2008/0112913 | A1 | 5/2008 | Librizzi et al. |
| 2008/0233061 | A1 | 9/2008 | Gates |
| 2008/0242573 | A1 | 10/2008 | Wei |
| 2009/0005449 | A1 | 1/2009 | Gunn et al. |
| 2009/0005460 | A1 | 1/2009 | Gunn et al. |
| 2009/0042765 | A1* | 2/2009 | Gizaw ............... D06M 13/463 510/516 |
| 2009/0311348 | A1 | 12/2009 | Einarsson et al. |
| 2010/0028376 | A1 | 2/2010 | Einarsson et al. |
| 2010/0158830 | A1 | 6/2010 | Wei et al. |
| 2010/0216707 | A1 | 8/2010 | Bernard et al. |
| 2010/0322878 | A1 | 12/2010 | Stella et al. |
| 2011/0038830 | A1 | 2/2011 | Bernard et al. |
| 2011/0091439 | A1 | 4/2011 | Bernard et al. |
| 2011/0257020 | A1 | 10/2011 | Stella et al. |
| 2011/0257030 | A1 | 10/2011 | Stella et al. |
| 2011/0280822 | A1 | 11/2011 | Griffin et al. |
| 2012/0009285 | A1* | 1/2012 | Wei ....................... A61K 8/447 424/757 |
| 2012/0184448 | A1 | 7/2012 | Stella et al. |
| 2012/0316095 | A1 | 12/2012 | Wei et al. |
| 2013/0149273 | A1 | 6/2013 | Wei et al. |
| 2016/0128913 | A1 | 5/2016 | Wei et al. |
| 2016/0128927 | A1 | 5/2016 | Wei et al. |
| 2017/0333315 | A1 | 11/2017 | Wei et al. |

FOREIGN PATENT DOCUMENTS

| | | |
|---|---|---|
| FR | 2908784 B1 | 5/2008 |
| FR | 2924613 B1 | 6/2009 |
| FR | 2924614 B1 | 6/2009 |
| FR | 2925314 B1 | 6/2009 |
| FR | 2924947 B1 | 3/2010 |
| GB | 2245585 A1 | 8/1992 |
| JP | H0395110 A | 4/1991 |
| JP | H04149112 A | 5/1992 |
| WO | WO9534280 A1 | 12/1995 |
| WO | WO2009081368 A2 | 7/2009 |

OTHER PUBLICATIONS

U.S. Appl. No. 16/120,681, filed Sep. 4, 2018, Karl Shiqing Wei.

International Search Report and Written Opinion of the International Searching Authority, PCT/US2011/039907, dated Feb. 16, 2012, 13 pages.

\* cited by examiner

METHODS OF SCREENING FOR MILD SKIN CLEANSER

FIELD OF THE INVENTION

Methods for screening skin cleansers for mildness can include utilization of a volume ratio of vesicles to micelles.

BACKGROUND OF THE INVENTION

Skin cleansers have been used for hundreds of years to cleanse skin and maintain personal hygiene. The plethora of ingredients that can be included in such cleansers creates a sliding scale of mildness from mild to very harsh. Consumer acceptance of a product can depend upon the consumer's perception of how well a cleanser cleans and whether that level of cleansing was appropriate. For example, a consumer may think that a cleanser cleans the skin very well, but that the level of cleansing is too intense, leaving the skin feeling dry. Such a cleanser would be found more toward the harsh end of the scale. As such, there is a need for a method of determining whether a skin cleanser would be considered mild.

SUMMARY OF THE INVENTION

A method of screening a skin cleanser for mildness, including: a) diluting with water a skin cleansing composition comprising a surfactant at a weight ratio of at least 5 parts water to 1 part surfactant forming a diluted cleansing composition; b) determining the amount of vesicles in the diluted cleansing composition; c) determining the amount of micelles in the diluted cleansing composition; and d) determining the volume ratio of vesicles to micelles in the diluted cleansing composition; wherein the skin cleansing composition is mild if the volume ratio of vesicles to micelles is greater than 50% at any dilution point of 5 parts water to 1 part cleansing surfactant or more.

This and other possible combinations will be explained in more detail below.

DETAILED DESCRIPTION OF THE INVENTION

Figure 1:
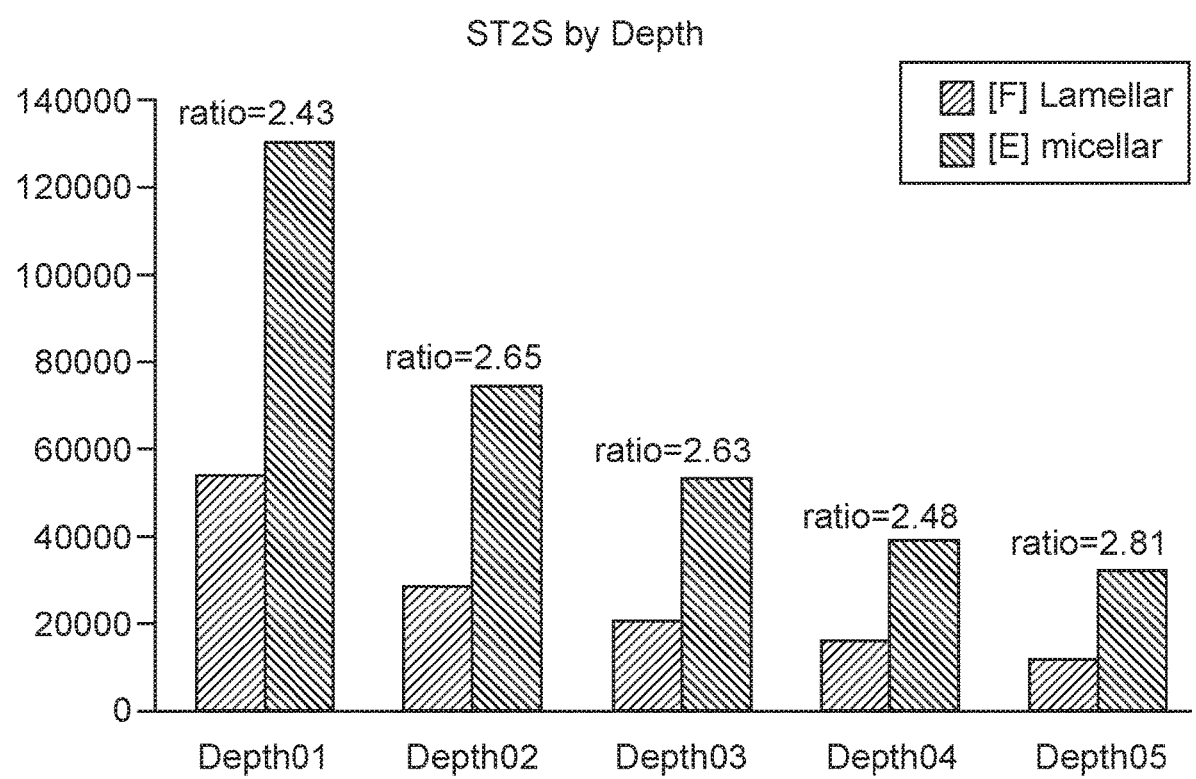
FIG. 1 is a graph showing the penetration of sodium trideceth-2 sulfate at 5 separate depths when in a micellar form versus a lamellar form.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

All measurements used herein are in metric units unless otherwise specified.

"Free of," as used herein, means the stated ingredient has not been added to the aerosol foam skin cleanser, but may incidentally form as a by-product or reaction product of the other components.

"Multiphase," when used with respect to skin cleansing compositions, refers to skin cleansing compositions comprising at least two chemically distinct phases (e.g., a structured cleansing phase and a benefit phase). Such phases can be in direct physical contact with one another. The phases of a multiphase skin cleansing composition can be blended or mixed to a significant degree, but still be physically distinct, like a dispersion. In these situations, the physical distinctiveness is often undetectable to the naked eye. When in a blended state, the phases are stable and do not significantly phase separate while sitting undisturbed. By no significant phase separation is meant that the composition does not need to be shaken prior to use. In addition, in the blended configuration, the phases are not in the form of an emulsion. The phases may also be in physical contact and visually distinct. Visually distinct phases can take many forms (e.g., phases can appear as striped, marbled). Again, visually distinct phases are stable, not phases that have separated upon standing and then need to be redispersed prior to use. The skin cleansing composition can also include a combination blended and visually distinct phases.

"Non-ionic low HLB Emulsifiers," as used herein, refers to non-ionic surfactants with HLB (hydrophilic and lipophilic balance) values from about 1.5 to about 13.

"STnS" refers to sodium trideceth(n) sulfate, wherein n can define the average number of moles of ethoxylate per molecule.

"Structured" as used herein with respect to a composition or a phase, means having a rheology that confers stability on the multiphase composition. The degree of structure is determined by characteristics determined by one or more of the following methods: the Young's Modulus Method, Yield Stress Method, or the Zero Shear Viscosity Method, all in the Test Methods section below. Accordingly, a surfactant phase is considered to be structured, if the phase has one or more of the following characteristics: a Yield Stress of greater than about 0.1 Pascal (Pa) to about 300 Pa; a Zero Shear Viscosity of at least about 500 Pascal-seconds (Pa-s) to about 10,000 Pa-s; and/or a Young's Modulus of greater than about 1 Pascal (Pa) to about 300 Pa.

"Vesicle," as used herein, means the surfactant colloid structure as spherical or ellipsoidal particle formed by enclosing a volume of aqueous solution in a surfactant bilayer. The vesicle can be in the form of one single bilayer or uni-lamellar vesicle, or the vesicle can be in the form with multiple surfactant bilayers or multi-lamellar vesicles. The vesicle diameter may range from a few nanometers to about ten micrometers.

Skin Cleansing Composition

Skin cleansers can come in many forms. These can include surfactant based cleansers. When looking at surfactant based cleansers, it can be hard to judge how much a cleansing composition will impact the skin. Consumers think of this as the mildness of the composition. While formulators can get an idea of the mildness of a composition based on the surfactant(s) being used in the composition, it has been discovered that the surfactant phase behavior (e.g., lamellar phase vs. micellar phase) of the composition itself can also impact the mildness (see FIG. 1).

One way to test the potential mildness of a surfactant is by looking at how it interacts with the skin. One type of interaction with the skin is skin penetration. Skin penetration looks at how much of the surfactant will penetrate into the skin. It is believed that the more the surfactant penetrates into the skin, the less mild the composition. Originally, this was believed to be largely driven by the structure of the surfactant, itself. Now, it is believed that the phase behavior associated with the surfactant can also have an impact on the penetration of the surfactant, and thus, its mildness.

One surfactant reviewed for mildness is sodium trideceth-2 sulfate. FIG. 1 shows a depth penetration chart for sodium trideceth-2 sulfate where the depth of penetration is represented with depth 01 to depth 05, depth 01 being the shallowest depth and depth 05 being the deepest depth. In FIG. 1, the lighter gray (left hand column) is sodium trideceth-2 sulfate deposited on skin in a vesicle form, specifically a lamellar form as part of Composition F (below), while the darker gray (right hand column) is sodium trideceth-2 sulfate deposited in a micellar form as part of Composition E (below). The compositions were applied in accordance with a forearm controlled application technique (FCAT), a description of which is found in Ertel et al., "A forearm controlled application technique for estimating the relative mildness of personal cleansing products," J. Soc. Cosmet. Chem., 46, 67-76 (March/April 1995). The levels of the target materials on the skin are then measured with a combination of liquid chromatography and mass spectrometry.

Figure 2:
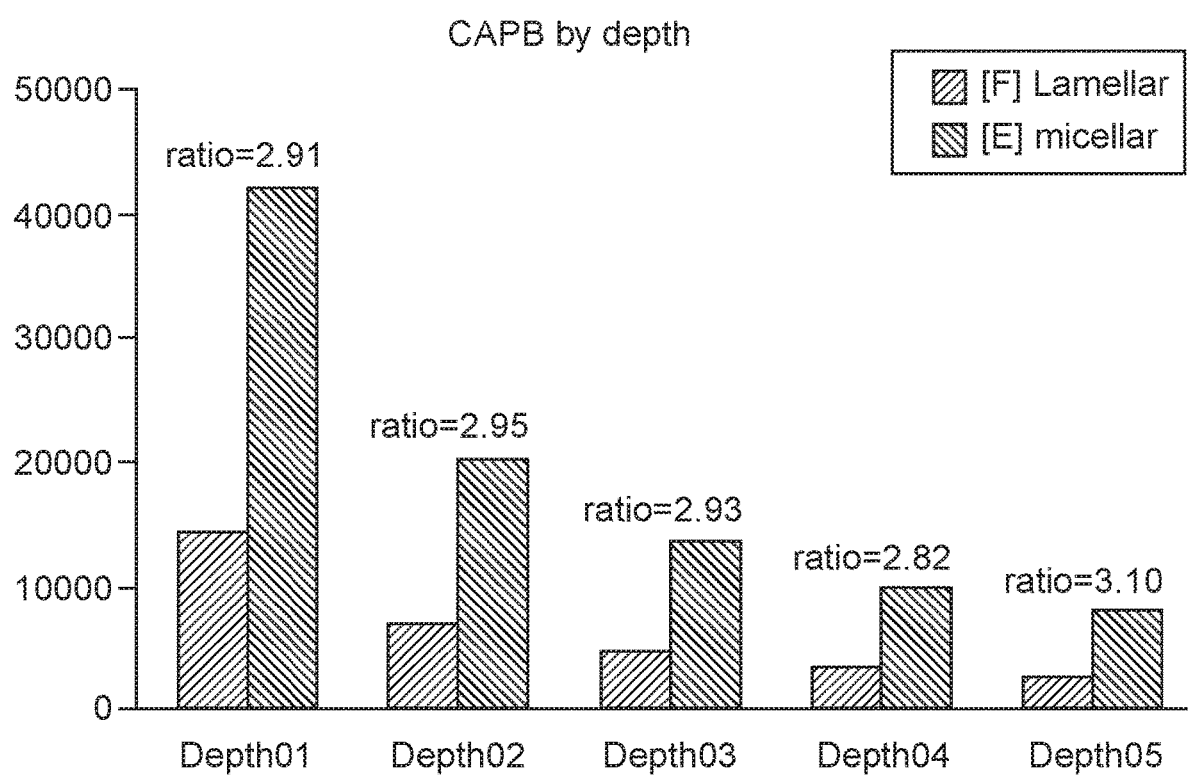
FIG. 2 is a graph showing the penetration of cocamidopropyl betaine at 5 separate depths when in a micellar form versus a lamellar form.
Figure 3:
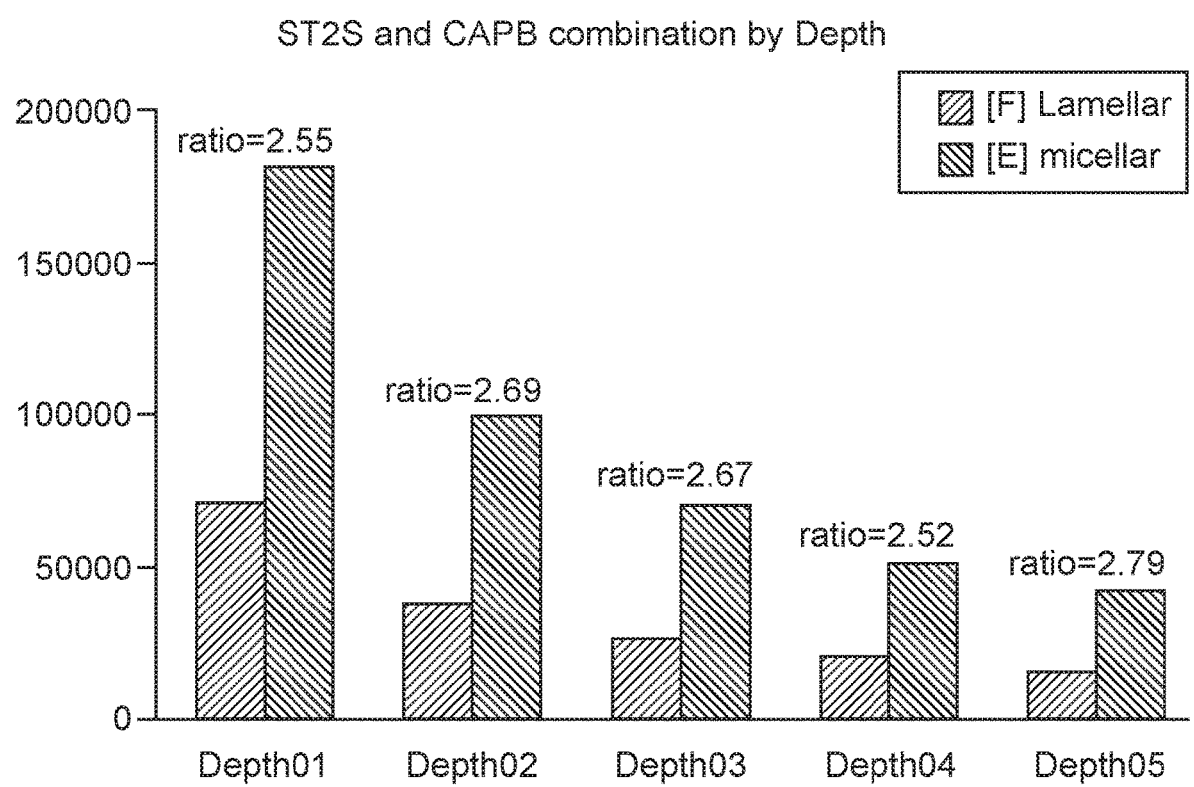
FIG. 3 is a graph showing the penetration of the combination of sodium trideceth-2 sulfate and cocamidopropyl betaine at 5 separate depths when in a micellar form versus a lamellar form.

As can be seen from FIG. 1, when deposited from a composition having micellar physical chemistry, sodium trideceth-2 sulfate penetrates the skin at a greater concentration at all 5 depths measured than when it is deposited from a composition with a lamellar physical chemistry. A similar result was seen with respect to cocamidopropyl betaine (CAPB) and with respect to the combination of sodium trideceth-2 sulfate and cocamidopropyl betaine as can be seen in FIGS. 2 and 3, respectively. As such, without being limited by theory, it is believed that incorporating surfactants into a composition which has at least a partial vesicle physical chemistry can have a positive impact on the mildness of the surfactant.

To further look at this phenomenon, several different formulations were reviewed for visual dryness and through corneometer measurements. The varying formulations along with their general descriptions, contained below in Tables A and B, were applied to the skin with the FCAT protocol noted above.

TABLE A

| | A | B | C | D | E | F |
|---|---|---|---|---|---|---|
| Water | 100% | Q.S. | Q.S. | Q.S. | Q.S. | Q.S. |
| Branched sodium trideceth-2-sulfate ST2S | — | 11.5% | 8.9% | 9.7% | 11.5% | 11.5% |
| Cocamidopropyl betaine | — | 3.5% | 2.70% | 2.9% | 3.5% | 3.5% |
| Trideceth-3 Iconal TDA-3-Ethoxylated Tridecyl Alcohol | — | 1.66% | 1.66% | 1.66% | — | 1.66% |
| Sodium Chloride | — | 4.75% | 4.75% | 4.75% | — | 4.75% |
| Guar, Hydroxypropyl Trimonium Chloride, N-Hance CG-17 | — | 0.39% | 0.3% | 0.32% | — | — |
| Acrylates/C10-30 Alkyl Acrylates Cross Polymer | — | 0.03% | 0.03% | 0.03% | — | — |
| Xanthan gum | — | 0.24% | 0.19% | 0.2% | — | — |
| Petrolatum | — | — | — | 9.8% | — | — |
| Soybean Oil | — | — | 6.79% | — | — | — |
| Monoglyceryl Monooleate | — | — | 0.07% | 0.2% | — | — |
| Butylated hydroxyltoluene (BHT) | — | — | 0.14% | — | — | — |
| Disodium EDTA | — | 0.16% | 0.16% | 0.16% | 0.16% | 0.16% |
| Sodium Benzoate | — | 0.33% | 0.33% | 0.33% | 0.33% | 0.33% |
| Preservative (Kathon CG) | — | 0.03% | 0.03% | 0.03% | 0.03% | 0.03% |
| Perfume | — | 1.25% | 1.25% | 1.25% | — | 1.25% |
| pH | — | 5.70 | 5.70 | 5.70 | 5.70 | 5.70 |
| Ratio of Vesicles to Micelles Vesicles Volume/(Vesicles Volume + Micelle Volume) | 0 | 100% | 100% | 100% | 0% | 100% |

TABLE B

| | |
|---|---|
| A | Water control |
| B | Lamellar Phase Base Chassis without Lipid |
| C | Lamellar Phase Base Chassis with SBO as Lipid |
| D | Lamellar Phase Base Chassis with PET a LIPID |
| E | Main Surfactant from Base Chassis (ST2S/CAPB) in Micellar Phase |
| F | Main Surfactant from Base Chassis (ST2S/CAPB) in Lamellar Phase |

Figure 4:
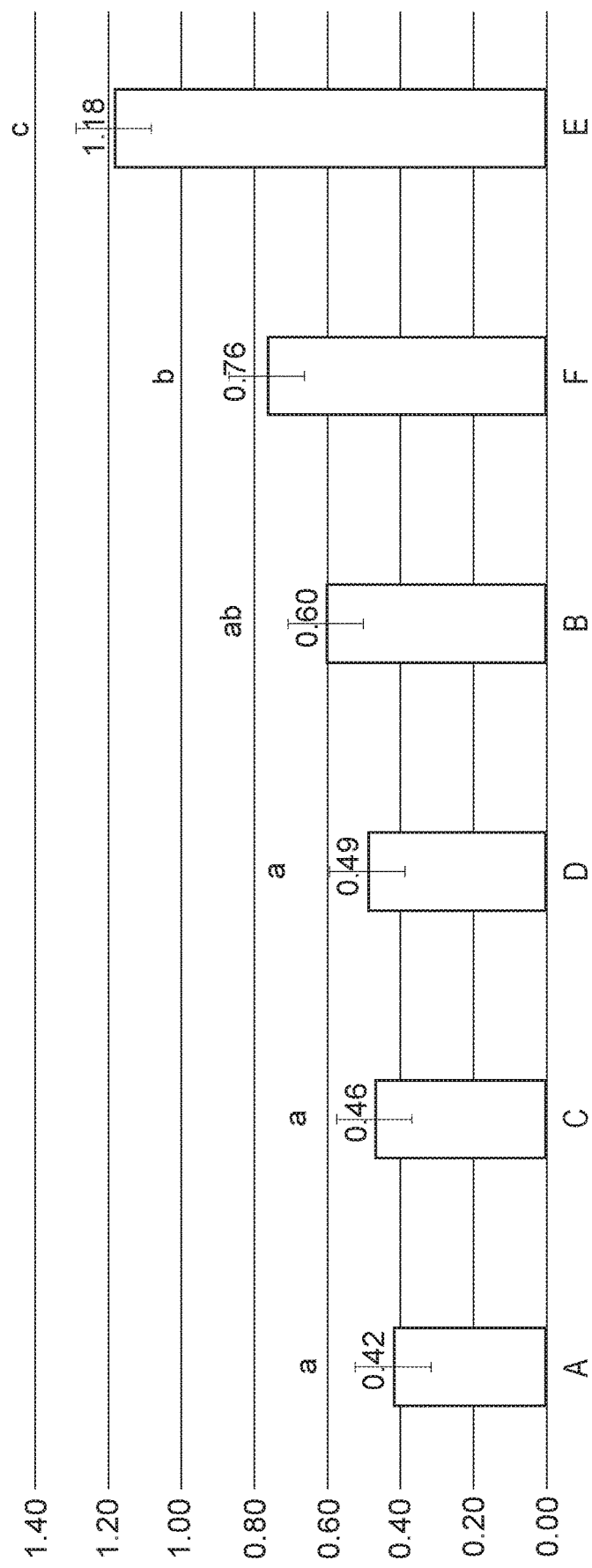
FIG. 4 is a graph showing the level of visual dryness of skin after application of the noted compositions.

The compositions were then evaluated for their visual dryness effect on skin by a qualified expert grader based on 0-6 scale, with a lower score indicating better skin condition. Visual dryness is an indication of the dryness of the skin versus a control, here water. The expectation is that products with a surfactant or soap cleanser will have some negative impact to skin dryness versus water, though, that can sometimes be counteracted when the composition contains and can deposit a benefit agent on the skin. As can be seen from FIG. 4, all the lamellar phase compositions (B, C, D and F) have significantly better skin dryness values vs. the same surfactant in the micellar phase (E).

Figure 5:
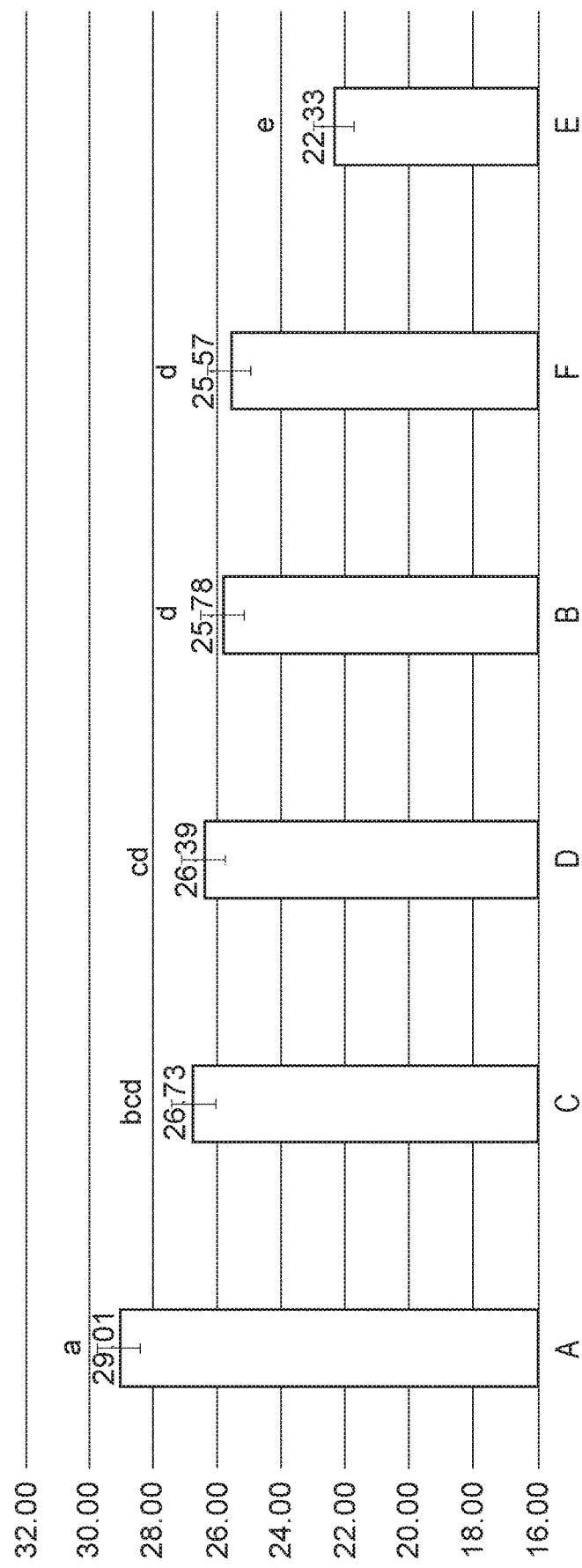
FIG. 5 is a graph showing the level of hydration of skin after application of the noted compositions as measured on a corneometer.

A corneometer can also be used as a way to determine the hydration level of the outer layers of the skin by looking at the skin's dielectric properties. The corneometer measurements were taken at the end of the FCAT study and the results can be found in FIG. 5. As can be seen from FIG. 5, all the lamellar phase compositions (B, C, D, and F) have significantly higher hydration vs. the same surfactant in the micellar phase (E).

In light of the above, it is believed that the volume ratio of vesicles to micelles can be used to identify cleansing compositions which will be milder in nature. So, when looking at a composition, one will want to understand the physical chemistry of that composition. There are several ways to evaluate a composition's physical chemistry, for example, dynamic light scattering, transmission electron microscopy, cryogenic transmission electron microscopy, nuclear magnetic resonance spectroscopy. Each of these methods has its advantages and disadvantages. While only two of these methods will be discussed in detail, it is believed any of these methods could be used.

First, with respect to dynamic light scattering, this method analyzes the size distribution of particles in a solution. In this method, a laser is directed through a sample, which scatters the light. The scattered light is captured by a photomultiplier tube. The intensity autocorrelation function is computed from the fluctuations in intensity of the scattered light. The decay of the intensity autocorrelation function is dependent on the particle diffusion coefficient, which in turn is related to the size of the particles in the suspension. Since vesicles and micelles differ considerably in size, the intensity autocorrelation function can only be fit with two different diffusion coefficients, and is weighted by the proportion of each. From this information, the volume fraction of vesicles and micelles can be determined. The micelles typically have diameters less than 7 nm while the vesicles typically have diameters larger than 7 nm, preferably the vesicles have diameters of 7 nanometers or more, or the majority (e.g. greater than 50%) of vesicles have a diameter of about 10 nanometers or more or the majority of vesicles have a diameter of about 20 nanometers or more or the majority of vesicles have a diameter of about 30 nanometers or more or the majority of vesicles have a diameter of about 40 nanometers, or more or the majority of vesicles have a diameter of about 50 nanometers or more.

The laser scattering technique is combined with the cryogenic transmission electron microscopy to confirm the assignment of the micelle vs. vesicles of the particles observed in the dynamic light scattering.

The cryogenic transmission electron microscopy method is a technique utilizing a beam of electrons transmitted through a thin sample to create an image of the sample. The image is created by the interaction of the electrons as they pass through the sample. The image can then be magnified and focused onto an imaging device for review. The image can capture very fine detail of the sample, like a single row of atoms. From this image, the structure of the particle is assigned as micelle or vesicle based on its size.

The volume intensity of the micelles is integrated in the dynamic light scattering. This integrated intensity of micelles is the total volume of the micelles ($V_{micelle}$). The volume intensity of the vesicles is integrated in the dynamic light scattering. This integrated intensity of vesicles is the total volume of the vesicles ($V_{vesicle}$). The volume ratio of vesicle to micelle is calculated as:

$$V_{vesicle}/(V_{vesicle}+V_{micelle}).$$

In addition to the presence of vesicles in a composition, the amount and/or type of vesicles in a composition can also impact its mildness. Within a composition, a vesicle can be in the form of uni-lamellar vesicle, a multi-lamellar vesicle, or there can be a combination of uni- and multi-lamellar vesicles. The differing forms of vesicles have differing degrees of structure. For example, a uni-lamellar vesicle, has smaller diameter than a multi-lamellar vesicle. It is believed that vesicles are less likely to penetrate into the skin due to their larger diameters vs. micelles. The multi-lamellar vesicles are expected to have better mildness profile vs. the uni-lamellar vesicles since the multi-lamellar vesicles are larger in diameter vs. uni-lamellar vesicles.

As noted above, the amount of vesicles within a composition can also impact its mildness. One way at examining the amount is to look at the volume ratio of vesicles to micelles. This can be determined as noted above and as specified below in the Methods section. It is believed that once a volume ratio of at least 50% is reached, a composition will have a noticeable increase in mildness over the same composition in a micellar form (i.e. with 0 volume fraction of vesicles). This noticeable increase can be determined, for example, by a statistically significant enhancement in the corneometer reading or visual dryness.

Skin Cleansing Compositions

A skin cleansing composition comprises a surfactant and a benefit agent. A skin cleanser can be multiphase, for example, having a cleansing phase and a benefit phase. A skin cleanser may have vesicles which are part of a phase. This phase could be lamellar and be uni-lamellar or multi-lamellar. The vesicles may be part of a cleansing phase. Vesicles, as noted above, are spherical or ellipsoidal particles formed by enclosing a volume of aqueous solution in a surfactant bilayer. The vesicle can be in the form of one single bilayer or uni-lamellar vesicle, or the vesicle can be in the form with multiple surfactant bilayers or multi-lamellar vesicles. The volume ratio of vesicles to micelles in a cleansing phase can be about 50% to about 100%; about 60% to about 100%; about 70% to about 100%; about 80% to about 100%; about 90% to about 100%, or about 100%.

A skin cleansing composition may comprise from about 50% to about 99%, by weight of the composition, of a cleansing phase, and from about 1% to about 50%, by weight of the composition, of a benefit phase. The skin cleansing composition itself, and/or any of its phases, may be structured.

Cleansing Phase

As noted herein, a skin cleansing composition can include a cleansing phase and a benefit phase. The cleansing phase can comprise one or more surfactants. Such surfactants can be suitable for application to skin and are compatible with other components of the cleansing phase, including water. A personal cleansing composition comprising the cleansing phase, can comprise, for example, from about 1% to about 30%, from about 5% to about 25%, or from about 15% to about 22%, by weight of the skin cleansing composition, of surfactant.

A cleansing phase can be structured. The structure may include, for example, a lamellar structure or phase. The lamellar phase may have a viscosity in the range of at least about 10,000 cps, at least about 20,000 cps, at least about 30,000 cps, or at least about 40,000 cps. One way to structure a phase or composition is through the use of a structured surfactant. A structured surfactant can include, for example, a branched anionic surfactant. Structured surfactants can include, for example, sodium trideceth(n) sulfate (STnS). For STnS, n defines the average moles of ethoxylation. n can range from about 0.5 to about 2.7, from about 1.1 to about 2.5, from about 1.8 to about 2.2, or n can be about 2. When n is less than 3, STnS can provide improved stability, improved compatibility of benefit agents within the skin cleansing compositions, and increased mildness of the skin cleansing composition.

Another way to structure a composition or phase is through the use of a structurant. The skin cleansing composition may comprise from about 0.1% to about 30%, from about 0.5% to about 20%, from about 0.5% to about 10%, or from about 0.5% to about 5%, by weight of the cleansing composition, of a structurant. The skin cleansing composition may comprise from about 0.1% to about 30%, from about 0.5% to about 20%, from about 0.5% to about 10%, or from about 0.5% to about 5%, by weight of the cleansing phase, of a structurant.

A structurant can be used to structure either the water or the surfactant of the cleansing phase. Non-limiting examples of inorganic water structurants for use in skin cleansing compositions can include silicas, clays such as a synthetic silicates (Laponite XLG® and Laponite XLS® from Southern Clay), or mixtures thereof. Non-limiting examples of charged polymeric water structurants for use in the skin cleansing composition can include Acrylates/Vinyl Isodecanoate Crosspolymer (Stabylen 30®. from 3V), Acrylates/Vinyl neodecanoate Crosspolymer (Aculyn 38® from Rohm and Haas) Acrylates/C10-30 Alkyl Acrylate Crosspolymer (Pemulen TR1® and TR2®), Carbomers, Ammonium Acryloyldimethyltaurate/VP Copolymer (Aristoflex AVC® from Clariant), Ammonium Acryloyldimethyltaurate/Beheneth-25 Methacrylate Crosspolymer (Aristoflex HMB® from Clariant), Acrylates/Ceteth-20 Itaconate Copolymer (Structure 3001® from National Starch), Polyacrylamide (Sepigel 305® from SEPPIC), or mixtures thereof.

Non-limiting examples of water soluble polymeric structurants for use in the skin cleansing composition include cellulosic gel, hydroxypropyl starch phosphate (Structure XL® from National Starch), polyvinyl alcohol, or mixtures thereof. Non-limiting examples of associative water structurants for use in the skin cleansing composition include synthetic and natural gums and thickeners such as xanthan gum (Ketrol CG-T® from CP Kelco), succinoglycan (Rheozan® from Rhodia, gellum gum, pectin, alginates, starches including pregelatinized starches, modified starches, or mixtures thereof.

Suitable lamellar structurants can include fatty acids or ester derivatives thereof, fatty alcohols, ethoxylated fatty alcohol, trihydroxystearin (available from Rheox, Inc. under the trade name THIXCIN®), polymethyacrylamidopropyl trimonium chloride (available from Rhodia under the trade name POLYCARE® 133), or a combination thereof. If the lamellar structurant is a fatty acid, or an ester of fatty acid, the hydrocarbon backbone can be straight chained or branched. In one example, the lamellar structurant is selected from lauric acid, fatty alcohols, ethoxylated fatty alcohols, Trihydroxystearin, or a combination thereof.

In addition to a structured surfactant and/or a structurant, a skin cleansing composition can include a cleansing surfactant. The cleansing surfactant may be anionic, amphoteric, zwitterionic, or a combination thereof. A skin cleansing composition can include from about 1% to about 30%, by weight of the skin cleansing composition, of a cleansing surfactant.

Examples of some suitable anionic cleansing surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, sodium cocoyl isethionate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, or a combination thereof.

Amphoteric cleansing surfactants can include those that can be broadly described as derivatives of aliphatic secondary and tertiary amines in which an aliphatic radical can be a straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate, N-higher alkyl aspartic acids, and combinations thereof. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic cleansing surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocamidopropyl betaine.

A cleansing phase can comprise a nonionic emulsifier. The nonionic emulsifier may be a low HLB emulsifier. These types of emulsifiers are generally seen as non-lathering, contributing more to structure than cleansing, and are therefore not counted in the amount of total surfactant. A low HLB non-ionic emulsifier has an HLB from about 1.5 to 13.0, from about 3.4 to 13.0, from about 3.4 to about 9.5, or from about 3.4 to about 8.0. The skin cleansing composition can comprise a nonionic emulsifier at concentrations ranging from about 0.1% to about 10%, from about 0.25% to about 8%, from about 0.5% to about 5%, from about 1.0% to about 3%, or from about 1.5% to about 2.5%, by weight of the skin cleansing composition.

The balance between the hydrophilic and lipophilic moieties in an emulsifier molecule is used as a method of classification (hydrophile-lipophile balance, HLB). The HLB values for commonly-used emulsifiers are readily available in the literature (e.g., HLB Index in *McCutcheon's Emulsifiers and Detergents*, MC Publishing Co., 2004). For example, cocamide monoethanolamine (CMEA) is known in the art to have an HLB value of 16.8. If no value is shown in the literature, an HLB value may be estimated by calculation. The HLB system was originally devised by Griffin (J. Soc. Cosmetic Chem., 1, 311, 1949). Griffin defined the HLB value of an emulsifier as the mol % of the hydrophilic groups divided by 5, where a completely hydrophilic molecule (with no non-polar groups) had an HLB value of 20.

Non-limiting examples of nonionic emulsifiers for use herein can comprise glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, or mixtures thereof.

A cleansing phase may also comprise an associative polymer. The cleansing phase can comprise from about 0.001% to about 5%, from about 0.005% to about 0.5%, from about 0.007% to about 0.05%, from about 0.008% to about 0.04%, or from about 0.01% to about 0.03%, by weight of the skin cleansing composition, of an associative polymer.

Such associative polymers can be crosslinked, alkali swellable, associative polymers comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in the presence of an electrolyte. The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains.

It has also been discovered that crosslinked, associative polymers having certain % HM and certain carbon numbers of hydrophobic end groups of alkyl side chains can provide significant enhancement of structure to skin cleansing compositions comprising a structured surfactant, especially to skin cleansing compositions comprising reduced levels of surfactant. Such associative polymers can also provide the above structure at low levels. Concentrations of associative polymers of about 5% or even 10% have been known to provide a sufficient amount structure. It has been discovered that when an associative polymer % HM and an alkyl side chain number of carbons can be optimized, the structure of a cleansing phase can be increased using less than about 3 wt %, less than about 2%, less than about 1%, and less than about 0.2%, of an associative polymer, as a weight percentage of the cleansing phase.

The acidic monomer can comprise any acid functional group, for example sulfate, sulfonate, carboxylate, phosphonate, or phosphate or mixtures of acid groups. The acidic monomer can comprise, for example, a carboxylate. Alternatively, the acidic monomer can be an acrylate, including acrylic acid and/or methacrylic acid. The acidic monomer can comprise a polymerizable structure, e.g., vinyl functionality. Mixtures of acidic monomers, for example acrylic acid and methacrylic acid monomer mixtures, may be useful as well.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth)acrylate is understood to mean either methyl acrylate or acrylate, or mixtures of the two.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% HM. Associative polymers can comprise about $C_{16}$ (cetyl) alkyl hydrophobic side chains with about 0.7% hydrophobic modification, but a percentage hydrophobic modification can be up to an aqueous solubility limit in surfactant containing compositions (e.g., up to 2%, 5%, or 10%). Other associative polymers can include stearyl, octyl, decyl, and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

A skin cleansing composition may also comprise a non-associative polymer. The skin cleansing composition can comprise from about 0.01% to about 5%, from about 0.05% to about 1%, from about 0.07% to about 0.5%, or from about 0.1% to about 0.3%, by weight of the skin cleansing composition, of a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), synthetic hydrocarbon polymers (e.g., polyacrylamide and copolymers, polyethylene oxide, polyacrylic acid copolymers), and combinations thereof.

A skin cleansing composition can also comprise a cationic deposition polymer. The cationic deposition polymer can be present in an amount of 0.1% to about 2%, by weight of the skin cleansing composition. Suitable cationic deposition polymers can contain cationic nitrogen-containing moieties such as quaternary moieties. Non-limiting examples of cationic deposition polymers can include polysaccharide polymers, such as cationic cellulose derivatives. Cationic cellulose polymers can be salts of hydroxyethyl cellulose reacted with trimethyl ammonium substituted epoxide, referred to in the industry (CTFA) as Polyquaternium 10, which can be available from Amerchol Corp. (Edison, N.J.) in their Polymer KG, JR, and LR series of polymers. Other suitable cationic deposition polymers can include cationic guar gum derivatives, such as guar hydroxypropyltrimonium chloride, specific examples of which can include the Jaguar® series commercially available from Rhodia Inc. and N-Hance® polymer series commercially available from Aqualon. Deposition polymers can have a cationic charge density from about 0.8 meq/g to about 2.0 meq/g or from about 1.0 meq/g to about 1.5 meq/g, or about 0.96 meq/g.

A cleansing phase may also include an electrolyte. Electrolytes may be present at a level of about 1% to about 10%, by weight of the skin cleansing composition. Suitable electrolytes can include anions such as phosphate, chloride, sulfate, citrate, and mixtures thereof and cations such as sodium, ammonium, potassium, magnesium, and mixtures thereof. For example, suitable electrolytes can include sodium chloride, ammonium chloride, sodium sulfate, ammonium sulfate, and mixtures thereof.

A cleansing phase may include water. The cleansing phase can comprise from about 10% to about 90%, from about 40% to about 85%, or from about 60% to about 80%, by weight of the skin cleansing composition, of water.

Benefit Phase

A skin cleansing composition may also comprise a benefit phase. The skin cleansing compositions can include two or more benefit phases. A benefit phase can be hydrophobic and/or anhydrous. A benefit phase can also be substantially free of or free of surfactant. A skin cleansing composition may include from about 3% to about 50%, by weight of the skin cleansing composition, of a benefit phase. Usually, the benefit phase is dispersed in the cleansing phase.

A benefit phase can comprise a hydrophobic benefit agent. A skin cleansing composition may include from about 0.1% to about 20%, by weight of the skin cleansing composition, of a hydrophobic benefit agent. A hydrophobic benefit agent can be insoluble in the cleansing phase. Suitable benefit agents can include, for example, petrolatum, monoglyceryl monooleate, mineral oil, glycerides (e.g., soybean oil), sucrose polyesters, lanolin, lanolin derivatives, lanolin esters, lanolin oil, natural waxes, synthetic waxes, volatile organosiloxanes, derivatives of volatile organosiloxanes, non-volatile organosiloxanes, derivatives of non-volatile organosiloxanes, natural triglycerides, synthetic triglycerides, and mixtures thereof.

SEFOSE® includes one or more types of sucrose polyesters. Sucrose polyesters are derived from a natural resource and therefore, the use of sucrose polyesters as the benefit agent can result in a positive environmental impact. Sucrose polyesters are polyester materials having multiple substitution positions around the sucrose backbone coupled with the chain length, saturation, and derivation variables of the fatty chains. Such sucrose polyesters can have an esterification ("IBAR") of greater than about 5. For example, the sucrose polyester may have an IBAR of about 5 to about 8. In another example, the sucrose polyester may have an IBAR of about 5-7; in another example, the sucrose polyester can have an IBAR of about 6. In yet another example, the sucrose polyester can have an IBAR of about 8. As sucrose polyesters can be derived from natural resources, a distribution in the IBAR and chain length may exist. For example, a sucrose polyester having an IBAR of 6 may contain a mixture of mostly IBAR of about 6, with some IBAR of about 5, and some IBAR of about 7. Additionally, such sucrose polyesters may have a saturation or iodine value ("IV") of about 3 to about 140. In another example, the sucrose polyester may have an IV of about 10 to about 120. In yet another example, the sucrose polyester may have an IV of about 20 to 100. Further, such sucrose polyesters may have a chain length of about $C_{12}$ to $C_{20}$.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio. Sucrose polyesters can also be combined with other benefit agents in the benefit phase.

Non-limiting examples of glycerides suitable for use as hydrophobic benefit agents herein can include castor oil, safflower oil, corn oil, walnut oil, peanut oil, olive oil, cod liver oil, almond oil, avocado oil, palm oil, sesame oil, soybean oil, vegetable oils, sunflower seed oil, vegetable oil derivatives, coconut oil and derivatized coconut oil, cottonseed oil and derivatized cottonseed oil, jojoba oil, cocoa butter, petrolatum, mineral oil, and combinations thereof.

Non-limiting examples of alkyl esters suitable for use as hydrophobic benefit agents herein can include isopropyl esters of fatty acids and long chain esters of long chain (i.e. $C_{10}$-$C_{24}$) fatty acids, e.g., cetyl ricinoleate, non-limiting examples of which can include isopropyl palmitate, isopropyl myristate, cetyl riconoleate, and stearyl riconoleate. Other examples can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic benefit agents herein can include oleyl myristate, oleyl stearate, oleyl oleate, and combinations thereof.

Non-limiting examples of polyglycerin fatty acid esters suitable for use as hydrophobic benefit agents herein can include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic benefit agents herein can include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic benefit agents herein can include dimethicone copolyol, dimethylpolysiloxane, diethylpolysiloxane, mixed $C_1$-$C_{30}$ alkyl polysiloxanes, phenyl dimethicone, dimethiconol, and combinations thereof. Still other suitable hydrophobic skin benefit agents can include milk triglycerides (e.g., hydroxylated milk glyceride) and polyol fatty acid polyesters.

Other Skin Cleansing Composition Materials

In addition to what has been described above, a skin cleansing composition may also include additional materials in any phase. These materials can include for example, perfume, colorants, antimicrobials, pH modifiers, and the like. Such materials are usually formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less, by weight of the skin cleansing composition.

Examples

|  | Inventive Ex. C | Inventive Ex. D |
| --- | --- | --- |
| Water | Q.S. | Q.S. |
| Branched sodium trideceth-2-sulfate ST2S | 8.9% | 9.7% |
| Cocamidopropyl betaine | 2.70% | 2.9% |
| Trideceth-3 Iconal TDA-3-Ethoxylated Tridecyl Alcohol | 1.66% | 1.66% |
| Sodium Chloride | 4.75% | 4.75% |
| Guar, Hydroxypropyl Trimonium Chloride, N-Hance CG-17 | 0.3% | 0.32% |
| Acrylates/C10-30 Alkyl Acrylates Cross Polymer | 0.03% | 0.03% |
| Xanthan gum | 0.19% | 0.2% |
| Petrolatum | — | 9.8% |
| Soybean Oil | 6.79% | — |
| Monoglyceryl Monooleate | 0.07% | 0.2% |
| Butylated hydroxyltoluene (BHT) | 0.14% | — |
| Disodium EDTA | 0.16% | 0.16% |
| Sodium Benzoate | 0.33% | 0.33% |
| Preservative (Kathon CG) | 0.03% | 0.03% |
| Perfume | 1.25% | 1.25% |
| pH | 5.70 | 5.70 |
| Ratio of Vesicles to Micelles Vesicles Volume/ (Vesicles Volume + Micelle Volume) | 100% | 100% |

Methods a. Dynamic Light Scattering (DLS) Method

A sample is placed in a glass jar with a lid. Where the sample has been stored or sitting for a day or more, the sample jar is gently inverted by hand for about 5 minutes to ensure the sample is homogenous. This is done carefully and as gently as possible to ensure the sample is exposed to minimal shear prior to subsequent processing and analysis.

The sample jar is opened and 1 mL of sample is transferred into a 20 mL glass sintering vial. 10 mL of hard water is pipetted into the same glass sintering vial. The amount of water can be adjusted so that the desired level of dilution for measurement can be used. A dilution point can be, for example, 5 parts water to 1 part cleansing surfactant, 7 parts water to 1 part cleansing surfactant, 9 parts water to 1 part cleansing surfactant, etc. Hard water can be simulated by combining 4.1 mg of calcium chloride dihydrate and 6.2 mg of magnesium chloride hexahydrate into 50 mL of deionized water. Once the water has been added to the sample, a 1 mL pipette is used to gently aspirate and pipette out the mixture leading to a homogeneous mixture of the dilute sample. Again, the sample was mixed gently to expose it to minimal shear.

A Fischer scientific vortex mixer is set to "on" at a rate of 3000 rpm. The sintering vial is then pushed against the vortex mixer for 30 seconds. Vortexing leads to a 2-phase system with the dilute fluid sample on the bottom of the vial and foam on the top. A 10 mL glass dynamic light scattering cuvette is prepared (or was previously prepared) by rinsing with deionized water and drying. 1 mL of the dilute sample is then taken from the bottom of the sintering vial and transferred into the prepared 10 mL glass dynamic light scattering (DLS) cuvette. The DLS cuvette is then placed into the sample cuvette holder of a Brookhaven Instruments BI-2000 laser light scattering system.

The DLS laser water-based coolant system is turned "on." The DLS laser is powered "on." The DLS laser is a Lexal Laser 95, 8 W Argon laser and is set to a power that provides a scattering light intensity reading at the sensor of 200 kilo counts per second. The angle between laser and scattering detector (i.e. the scattering angle) is set using Brookhaven Instruments DLS software and a motorized goniometer stage (part of the BI-2000 DLS System). An angle of 120° was found to be optimal for detection of micelles and vesicles. Discrete scattering angles of 100° 110°, 120° and 130° were used for all the measurements.

The intensity autocorrelation function is developed, from which the particle size distribution is obtained. These two operations are part the software supplied by Brookhaven Instruments with the DLS The volume intensity of the micelles is integrated in the dynamic light scattering. This integrated intensity of micelles is the total volume of the micelles ($V_{micelle}$). The volume intensity of the vesicles is integrated in the dynamic light scattering. This integrated intensity of vesicles is the total volume of the vesicles ($V_{vesicle}$). The volume ratio of vesicle to micelle is calculated as:

$$V_{vesicle}/(V_{vesicle}+V_{micelle}).$$

b. Cryogenic Transmission Electron Microscopy (Cryo TEM) Method

The following Cryogenic Transmission Electron Microscopy Method is performed to confirm the structure of the particles and assignment of particles/objects as micelle vs. vesicles observed in the DLS Method.

A sample is placed in a glass jar with a lid. Where the sample has been stored or sitting for a day or more, the sample jar is gently inverted by hand for about 5 minutes to ensure the sample is homogenous. This is done carefully and as gently as possible to ensure the sample is exposed to minimal shear prior to subsequent processing and analysis.

The sample jar is opened and 0.3 mL of sample is transferred into a 20 mL glass sintering vial. 2.7 mL of hard water is pipetted into the same glass sintering vial. The amount of water can be adjusted so that the desired dilution point for measurement can be used. A dilution point can be, for example, 5 parts water to 1 part cleansing surfactant, 7 parts water to 1 part cleansing surfactant, 9 parts water to 1 part cleansing surfactant, etc. Hard water can be simulated by combining 4.1 mg of calcium chloride dihydrate and 6.2 mg of magnesium chloride hexahydrate into 50 mL of deionized water.

A Fischer scientific vortex mixer is set to "on" at a rate of 3000 rpm. The sintering vial is then pushed against the vortex mixer for 15 seconds. Vortexing leads to a 2-phase system with the dilute fluid sample on the bottom of the vial and foam on the top. 5 µL of the dilute sample is then taken from the bottom of the sintering vial and transferred onto a TEM sample grid which was a 3 mm, 200 mesh, copper grid with a lacy carbon film. The TEM sample grid is then prepared by removing any excess of the diluted sample to ensure a sample thickness of 10-100 nm. The sample is thinned using a 10 µL glass microcapillary. After removal of the excess sample is complete, the TEM sample grid is placed in liquid ethane long enough to vitrify the sample. Vitrified samples are stored in liquid nitrogen until ready for analysis.

The sample grid is removed from the liquid nitrogen and transferred to a Gatan 626 cryogenic transfer holder through the use of a Gatan cryogenic workstation. The Gatan 626 transfer holder is then used to transfer the sample grid into a JEM-2100 LaB6 Transmission Electron Microscope for imaging. Samples are imaged with high tension set at 200 kV, 105 μA. Vesicles and micelles in the images are counted to estimate the volume of vesicles and micelles and volume ratio of vesicle to micelle per the formula above in the DLS Method. This Cryo TEM Method provides direct images that are visible, for fewer particles/objects, whereas the DLS Method is an "inferred" measurement on many more particles/objects. Thus the Cryo TEM Method is complementary to the DLS Method and confirms proper assignment of particles/objects as vesicles versus micelles.

c. Yield Stress, Young's Modulus, and Zero Shear Viscosity Methods

The Zero Shear Viscosity of a material which is a phase or a component of the skin cleansing composition, can be measured either prior to combining in the skin cleansing composition, after preparing a composition, or first separating a phase or component from a personal care composition by suitable physical separation means, such as centrifugation, pipetting, cutting away mechanically, rinsing, filtering, or other separation means. The timing of the measurement can depend on what is available. For example, if a final product is all that is available and a phase of the product is the target for measurement, then the phase will be separated prior to measurement.

A controlled stress rheometer such as a TA Instruments AR2000 Rheometer is used to determine the Yield Stress and Zero Shear Viscosity. The determination is performed at 25° C. with a 4 cm diameter parallel plate measuring system and a 1 mm gap. The geometry has a shear stress factor of 79580 m-3 to convert torque obtained to stress. Serrated plates can be used to obtain consistent results when slip occurs.

First, the target material is positioned on a rheometer base plate; the measurement geometry (upper plate) is moved into position 1.1 mm above the base plate. Excess material at the geometry edge is removed by scraping after locking the geometry. The geometry is then moved to the target 1 mm position above the base plate and a pause of about 2 minutes is allowed to allow loading stresses to relax. This loading procedure ensures no tangential stresses are loaded at the measurement onset which can influence the results obtained. If the material comprises particles discernible to the eye or by feel (e.g., beads) that are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty measurement points per decade of stress increase are obtained. Stress, strain, and viscosity are recorded. If the measurement result is incomplete, for example, if material is observed to flow from the gap, results obtained are evaluated with incomplete data points excluded. If there are insufficient points to obtain an accurate measurement, the measurement is repeated with increased number of sample points.

The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)} = m * \text{Log(stress)} + b \quad (1).$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., 10.sup.x for each x). The predicted strain is compared to the actual strain at each measurement point to obtain a % variation at each point, using Equation (2). % variation=100*(measured strain-predicted strain)/measured strain (2).

The Yield Stress is the first stress (Pa) at which % variation exceeds 10% and subsequent (higher) stresses result in even greater variation than 10% due to the onset of flow or deformation of the structure.

The Young's Modulus (Pa) is obtained by graphing Stress (Pa) vs. Strain (unitless) and obtaining a slope of a regression line of an initial linear region between Stress vs. Strain, typically occurring in the region below about 4% strain. If the relationship is not linear, the linear regression line slope below 2% strain is taken as the Young's Modulus (Pa), using unitless strain.

The Zero Shear Viscosity is obtained by taking a first median value of viscosity in Pascal-seconds (Pa-s) for viscosity data obtained between and including 0.1 Pa and a point where viscosity begins to steeply decline. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

As set forth above, a phase or composition can be considered to be structured if it has a Zero Shear Viscosity of about 500 Pascal-seconds (Pa-s) to about 10,000 Pa-s, a Yield Stress of greater than about 0.1 Pascal (Pa) to about 300 Pa, and/or a Young's Modulus of greater than about 1 Pascal (Pa) to about 300 Pa.

d. Corneometer Method

Once the materials are applied as desired for evaluation, skin hydration can be measured with a Corneometer, while baseline measurements are taken prior to application of materials. In particular, skin hydration based upon measurements of capacitance can be assessed using the Corneometer® 825. Such use of a Corneometer is set forth in U.S. Pat. No. 9,671,410. Such measurements can be non-invasive and can be taken in duplicate on each site of the application surface at the time(s) selected as relevant, for example: at baseline, prior to $1^{st}$ treatment; 3 hours post $1^{st}$, $3^{rd}$, $5^{th}$ $14^{th}$ and $21^{st}$ treatments; 24 hours post $4^{th}$, $13^{th}$ and $21^{st}$, treatments, 48 hours post $21^{st}$ treatment after a visual assessment has been completed. Subjects can be acclimated for a minimum of thirty minutes in an environmentally controlled room (maintained at 70° F.±2 and 30-45% relative humidity)

prior to the non-invasive instrumental measurements taken on the treatment site. Data can be recorded electronically using a Sponsor's direct data entry and data capture programs. Measurements can be performed according to a test facility's standard operating procedures and/or the Sponsors Instrument Operation Manual.

The Corneometer values are arbitrary units for electrical impedance. At baseline, for subjects having a dry skin grade from about 2.5 to about 4.0, an adjusted mean of such Corneometer values can typically fall within a range of about 15 to about 20. Higher Corneometer values can correspond to a higher hydration level, and thus, lower Corneometer values can correspond to lower hydration levels.

The instrument should only be operated by trained operators. Further, the same instrument(s) and operator(s) can be used throughout the study. Kimwipes can be used to wipe an end of a probe. The probe can be wiped with a Kimwipe between each measurement. At the end of an evaluation session, data collected for that period can be backed up according to instructions in the Sponsors Instrument Operation Manual, and a hard copy of the data can be printed.

"Combinations"

A. A method of screening a skin cleanser for mildness, comprising: a) diluting a skin cleansing composition comprising a cleansing surfactant with water at a weight ratio of at least 5 parts water to 1 part cleansing surfactant forming a diluted cleansing composition; b) determining the amount of vesicles in the diluted cleansing composition; c) determining the amount of micelles in the diluted cleansing composition; d) determining the volume ratio of vesicles to micelles in the diluted cleansing composition; and wherein the skin cleansing composition is mild if the volume ratio of vesicles to micelles is greater than 50% at any dilution point of 5 parts water to 1 part cleansing surfactant or more.

B. The method of paragraph A, wherein the size and volume of vesicles are determined using the DLS Method and the Cryo TEM Method.

C. The method of any of paragraphs A-B, wherein at least part of the vesicles are in the form of a lamellar phase.

D. The method of paragraph C, wherein at least part of the vesicles are in the form of a multi-lamellar phase.

E. The method of any of paragraphs A-D, wherein the skin cleansing composition comprises a cleansing phase comprising the cleansing surfactant and a benefit phase comprising a benefit agent.

F. The method of paragraph E, wherein the skin cleansing composition further comprises a structured surfactant.

G. The method of paragraph F, wherein the skin cleansing composition comprises from about 3% to about 20%, by weight of the skin cleansing composition, of the structured surfactant.

H. The method of any of paragraphs F-G, wherein the structured surfactant comprises sodium trideceth-2 sulfate.

I. The method of any of paragraphs A-H, wherein the cleansing phase further comprises a structurant.

J. The method of paragraph I, wherein the structurant comprises lauric acid, fatty alcohol, ethoxylated fatty alcohol, trihydroxystearin, or a combination thereof.

K. The method of any of paragraphs E-J, wherein the benefit agent comprises petrolatum, soy bean oil, sucrose polyester, monoglyceryl monooleate, or a combination thereof.

L. The method of any of paragraphs A-K, wherein the skin cleansing composition further comprises a non-ionic low HLB emulsifier.

M. The method of paragraph L, wherein the low HLB emulsifier comprises trideceth-3.

N. The method of any of paragraphs A-M, wherein the volume ratio of vesicles to micelles is greater than 80%.

O. The method of any of paragraphs A-N, wherein the dilution point is 5 parts water to 1 part cleansing surfactant, preferably 9 parts water to 1 part cleansing surfactant.

P. The method of any of paragraphs A-O, wherein the vesicles have a diameter of 7 nanometers or more.

Q. The method of any of paragraphs A-P, wherein the majority of vesicles have a diameter of about 10 nanometers or more.

R. The method of any of paragraphs A-Q, wherein the majority of vesicles have a diameter of about 30 nanometers or more.

S. The method of any of paragraphs A-R, wherein the majority of vesicles have a diameter of about 40 nanometers or more.

T. The method of any of paragraphs A-S, wherein the majority of vesicles have a diameter of about 50 nanometers or more.

U. Use of vesicles of 7 nanometers or more, preferably 10 nanometers or more, preferably 20 nanometers or more, more preferably 30 nanometers or more, at a volume ratio of vesicles to micelles of 50% or more in a cleansing composition comprising a cleansing surfactant to formulate a mild cleansing composition, wherein the volume ratio is determined on the cleansing composition at a dilution point of 5 parts water to 1 part cleansing surfactant.

V. Use of paragraph U, wherein the volume ratio is determined utilizing the Dynamic Light Scattering Method and the Blotless Cryogenic Transmission Electron Microscopy Method.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of screening a skin cleansing composition for mildness, comprising:
   a) providing a skin care composition comprising a cleansing surfactant;
   b) diluting the skin cleansing composition with water to form a diluted cleansing composition that has a weight ratio of at least 5 parts water to 1 part cleansing surfactant;
   c) determining the amount of vesicles in the diluted cleansing composition;
   d) determining the amount of micelles in the diluted cleansing composition; and
   e) determining the volume ratio of vesicles to micelles in the diluted cleansing composition;
   identifying the skin cleanser as mild if the volume ratio of vesicles to micelles is greater than 50% at any dilution point of 5 parts water to 1 part cleansing surfactant or more.

2. The method of claim 1, wherein the volume ratio of vesicles to micelles is determined using the DLS Method and the Cryo TEM Method.

3. The method of claim 1, wherein at least part of the vesicles are in the form of a lamellar phase.

4. The method of claim 3, wherein at least part of the vesicles are in the form of a multi-lamellar phase.

5. The method of claim 1, wherein the skin cleansing composition comprises a cleansing phase comprising the cleansing surfactant and a benefit phase comprising a benefit agent.

6. The method of claim 5, wherein the skin cleansing composition further comprises a structured surfactant.

7. The method of claim 6, wherein the skin cleansing composition comprises from about 3% to about 20%, by weight of the skin cleansing composition, of the structured surfactant.

8. The method of claim 7, wherein the structured surfactant comprises sodium trideceth-2 sulfate.

9. The method of claim 1, wherein the cleansing phase further comprises a structurant.

10. The method of claim 9, wherein the structurant comprises lauric acid, fatty alcohol, ethoxylated fatty alcohol, trihydroxystearin, or a combination thereof.

11. The method of claim 1, wherein the benefit agent comprises petrolatum, soy bean oil, sucrose polyester, monoglyceryl monooleate, or a combination thereof.

12. The method of claim 1, wherein the volume ratio of vesicles to micelles is greater than 80%.

13. The method of claim 1, wherein the majority of vesicles have a diameter of about 10 nanometers or more.

14. The method of claim 1, wherein the majority of vesicles have a diameter of about 20 nanometers or more.

15. The method of claim 1, wherein the majority of vesicles have a diameter of about 30 nanometers or more.

16. The method of claim 1, wherein the majority of vesicles have a diameter of about 40 nanometers or more.

17. The method of claim 1, wherein the majority of vesicles have a diameter of about 50 nanometers or more.

* * * * *